US011661438B2

United States Patent
Nadkarni et al.

(10) Patent No.: US 11,661,438 B2
(45) Date of Patent: May 30, 2023

(54) PURIFICATION OF ANTIBODY DRUG CONJUGATES USING A SODIUM PHOSPHATE GRADIENT

(71) Applicant: PFIZER INC., New York, NY (US)

(72) Inventors: Durgesh V. Nadkarni, Old Lyme, CT (US); Jeffry R. Borgmeyer, St. Louis, MO (US); He Meng, Newton, MA (US); Qingping Jiang, New Windsor, NY (US)

(73) Assignee: Pfizer, Inc., New York, NY (US)

( * ) Notice: Subject to any disclaimer, the term of this patent is extended or adjusted under 35 U.S.C. 154(b) by 779 days.

(21) Appl. No.: 15/778,290

(22) PCT Filed: Dec. 7, 2016

(86) PCT No.: PCT/IB2016/057417
§ 371 (c)(1),
(2) Date: May 23, 2018

(87) PCT Pub. No.: WO2017/109619
PCT Pub. Date: Jun. 29, 2017

(65) Prior Publication Data
US 2019/0367556 A1    Dec. 5, 2019

Related U.S. Application Data

(60) Provisional application No. 62/270,174, filed on Dec. 21, 2015.

(51) Int. Cl.
*C07K 1/18* (2006.01)
*C07K 1/22* (2006.01)
*A61K 47/68* (2017.01)

(52) U.S. Cl.
CPC ............ *C07K 1/18* (2013.01); *A61K 47/6811* (2017.08); *A61K 47/6849* (2017.08)

(58) Field of Classification Search
None
See application file for complete search history.

(56) References Cited

U.S. PATENT DOCUMENTS

| | | | | |
|---|---|---|---|---|
| 2013/0197198 A1* | 8/2013 | Sun | ...................... | C07K 16/065 530/387.3 |
| 2015/0353598 A1* | 12/2015 | Gagnon | ................... | C07K 1/18 530/387.1 |
| 2016/0051695 A1* | 2/2016 | Lin | .................... | A61K 47/6817 424/179.1 |
| 2017/0159099 A1* | 6/2017 | Beam | ........................ | C12Q 1/26 |

FOREIGN PATENT DOCUMENTS

| | | | | |
|---|---|---|---|---|
| WO | 2005044856 A2 | 5/2005 | | |
| WO | WO-2009017491 A1 * | 2/2009 | ............... | C07K 1/18 |
| WO | 2013072813 A2 | 5/2013 | | |
| WO | 2014072987 A1 | 5/2014 | | |
| WO | WO-2015195904 A1 * | 12/2015 | ......... | A61K 47/6889 |

OTHER PUBLICATIONS

Gagnon et al., "Antibody Aggregate Removal by Hydroxyapatite Chromatography", 2009, 440-446, 10(4).
Giovannini et al., "Isolation of a Recombinant Antibody from Cell Culture Supernatant: Continuous Annular Versus Batch and Expanded-Bed Chromatography", Biotechnology & Bioengineering, 2001, 522-529, 73(6).
Hamblett et al., "Effects of Drug Loading on the Antitumor Activity of a Monoclonal Antibody Drug Conjugate", Clinical Cancer Research, 2004, 7063-7070, 10.
Steindli et al., "A simple method to quantify staphylococcal protein A in the presence of human or animal IgG in various samples", 2000, 61-69, 235.
Tarditi et al., "Selective high-performance liquid chromatographic purification of bispecific monoclonal antibodies", Journal of Chromatography, 1992, 13-20, 599.
Shepard et al., "Discoloration of ceramic hydroxyapatite used for protein chromatography", Journal of Chromatography A, 2000, 93-98, 891.
Vola et al., "Comparison of Two Different HPLC Hydroxylapatite Matrices for Resolution of IgG Idiotypes", BioTechniques, 1993, 14(4).
Stanker et al., "One-Step Purification of Mouse Monoclonal Antibodies from Ascites Fluid by Hydroxylapatite Chromatography*", Journal of Immunological Methods, 1985, 157-169, 76.
International Search Report dated Mar. 8, 2017 for International Application No. PCT/IB2016/057417, filed Dec. 7, 2016.
Written Opinion of the International Searching Authority for International Application No. PCT/IB2016/057417, filed Dec. 7, 2016.

* cited by examiner

Primary Examiner — Daniel E Kolker
Assistant Examiner — James L Rogers
(74) Attorney, Agent, or Firm — Saul Ewing LLP (57) ABSTRACT

Methods of removing high molecular weight species, in particular aggregates, from antibody drug conjugate preparations, by contacting preparations of the antibody drug conjugate reaction mixture with a hydroxyapatite resin and selectively eluting the ADC from the resin using a gradient comprising sodium phosphate.

16 Claims, 6 Drawing Sheets

PURIFICATION OF ANTIBODY DRUG CONJUGATES USING A SODIUM PHOSPHATE GRADIENT

CROSS-REFERENCE TO RELATED APPLICATIONS

This application is a 35 U.S.C. § 371 national stage application of, and claims priority to, International Patent Application No. PCT/IB2016/057417, filed Dec. 7, 2016, which claims priority under 35 U.S.C. § 119(e) to U.S. Provisional Application No. 62/270,174, filed Dec. 21, 2015, all of which applications are is-incorporated herein by reference in their entireties.

FIELD OF THE INVENTION

The present invention relates to the chromatographic purification of antibody-drug conjugate (ADC) monomers from aggregates, and from other impurities typically formed in the process of making ADCs, by eluting an ADC preparation through a hydroxyapatite resin column using a sodium phosphate buffer, typically of varying concentration, to obtain purified ADC.

BACKGROUND

It is desirable to identify useful methods of purifying biomolecules (including proteins, peptides antibodies, fragments of proteins and antibodies and antibody-drug conjugates) that do not destroy or significantly reduce the biological activity of these molecules.

The production of ADCs typically involves the conjugation of one or more small molecule "payloads" (often a cytotoxic agent) to an antibody via a chemical linker. The conjugation process is designed to produce ADC monomers, which monomers comprise a single antibody linked to one or more payloads. However, impurities are often found in the product ("ADC preparation") of the ADC conjugation process. These impurities are known to include low molecular weight species (relative to the desired ADC monomer species) comprising mainly unconjugated antibody, unconjugated or "free" payload and also species such as solvents. These impurities are also known to include high molecular weight species (sometimes called HMWS, or high molecular mass species—HMMS) such as aggregates.

The presence of high levels of aggregates adversely affects product safety by causing complement activation or anaphylaxis upon administration. Aggregate formation may also hinder manufacturing processes by causing decreased product yield and loss of activity. Thus aggregates must be substantially removed from ADC preparations before those ADC preparations are able to be used in therapeutic applications, or in related studies.

The most common purification methods for protein conjugate preparations, such as antibody drug conjugate preparations, are predicated on differences in the size, charge, and/or solubility between the protein or protein-based molecules to be purified as compared to potential impurities. Protocols based on these parameters include but are not limited to affinity chromatography, ion exchange chromatography, size exclusion chromatography, and hydrophobic interaction chromatography. These chromatographic methods, however, may present technical difficulties in the separation of aggregated or multimeric species of antibodies or antibody drug conjugates. Techniques such as ion-exchange and hydrophobic interaction chromatography, for instance, may actually induce the formation of aggregates during purification due to an increased protein concentration or the required changes in buffer concentration and/or pH during elution. Further, in several instances, monomeric antibodies and corresponding aggregated antibodies show differences in isoelectric points that are too small to allow for their separation by ion-exchange chromatography. Tarditi, *J. Immunol. Methods* 599:13-20 (1992). Moreover, size exclusion chromatography is cumbersome and results in the significant dilution of the antibody drug conjugate monomeric product, which is a hindrance in large-scale, efficiency-based manufacturing processes. Leakage of ligands from affinity chromatography columns can also occur, which results in undesirable impurities in the eluted product. Steindl, *J. Immunol. Methods* 235:61-69(2000).

More generally, across various chromatographic methods, harsh elution conditions, when used in an attempt to break the tight binding of a protein or ADC to a matrix, are known to destroy the biological activity of the protein or ADC.

In the case of anti-Notch 3 ADCs of the type disclosed in WO2014/072987 (which is hereby incorporated by reference in its entirety), for instance the Notch3 ADC:

(where X is an anti-Notch 3 antibody) attempts to remove impurities comprising aggregates from anti-Notch 3 ADC preparations using anion exchange chromatography, cation exchange chromatography, as well as hydrophobic interaction chromatography have been found to be cumbersome and/or inefficient, as none of these methods as practiced were able to substantially and efficiently remove the aggregates from the anti-Notch 3 ADC preparations while maintaining the desired drug to antibody ratio (DAR) of the anti-Notch 3 ADC at between 3 and 5, preferably about 4 The ADC mixture with the average DAR of about 4 has been shown to afford the best therapeutics index in in-vivo and in-vitro models for some ADCs. Hamblett et al., *Effects of drug loading on the antitumor activity of a monoclonal antibody drug conjugate*, Clin Cancer Res 10:7063-7070 (2004).

Hydroxyapatite resin is composed of an insoluble calcium phosphate which forms both the matrix and the ligand. *Current Pharmaceutical Biotechnology.* 10 (4) pp. 440-6; 2009. Kevin Beam, Gagnon, Pete. *Validated Biosystems*, San Clemente, Calif. 92672, USA.

Functional groups consist of pairs of positively charged calcium ions (C-sites) and clusters of negatively charged phosphate groups (P-sites). The interactions between hydroxyapatite and proteins are complex and multi-mode. In one method of interaction, however, positively charged amino groups on proteins associate with the negatively charged P-sites and protein carboxyl groups interact by coordination complexation to C-sites. Shepard, S. *J. of Chromatography* 891:93-98(2000). Crystalline hydroxyapatite was the first type of hydroxyapatite used in chromatography, but it was limited by structural difficulties. Ceramic hydroxyapatite (cHA) chromatography was developed to overcome some of the difficulties associated with crystalline hydroxyapatite, such as limited flow rates. Ceramic hydroxyapatite has high durability, good protein binding capacity, and can be used at higher flow rates and pressures than crystalline hydroxyapatite. Vola et al., *BioTechniques* 14:650-655 (1993).

Hydroxyapatite chromatography has been attempted in the separation of proteins (such as antibodies) and nucleic acids. In such attempts the column may be equilibrated, and the sample applied, in a low concentration of phosphate buffer and the adsorbed proteins are then eluted in a concentration gradient of either a sodium chloride or a phosphate buffer (sodium or potassium phosphate buffer). See, e.g., Giovanni, *Biotechnology and Bioengineering* 73:522-529 (2000), particularly at pages 524-525 ("antibody peak contained several impurities"); and Stanker, J. *Immunological Methods* 76:157-169(1985). However, such attempts to use phosphate gradients to separate monoclonal antibodies (mAbs) particularly for IgGs have been less effective, resulting in poor resolution and a failure to remove impurities. Sodium chloride buffers and gradients in addition to phosphate buffers have been shown to be somewhat more effective in purification of mAbs (WO2005/044856).

Despite the use of hydroxyapatite resin to separate antibodies, this material has not previously been used successfully to purify ADCs including the Notch 3 ADCs of the type disclosed in WO2014/072987. Attempts at purification of ADCs by employing different gradients of sodium chloride buffer during elution have been ineffective at removing aggregate impurities from ADC preparations, and phosphate buffers and gradients, having been shown ineffective in purification of mAbs (particularly IgGs), were not expected to effectively remove aggregate impurities. Thus, there is need for efficient methods of removing aggregate impurities from ADC preparations which methods do not destroy the biological activity of the desired ADC monomers.

SUMMARY OF THE INVENTION

Surprisingly, it has been found that a novel phosphate gradient can be used in a hydroxyapatite chromatography method for the purification of ADC monomers from aggregate impurities by selectively removing aggregates, as well as low molecular weight impurities like organic solvents and unconjugated ("free") payload. Thus, the present invention relates to methods of removing aggregates from ADC monomers in ADC preparations, by contacting such ADC preparations with a hydroxyapatite resin and selectively and separately eluting the aggregates and ADC monomers from the resin using a gradient of sodium phosphate.

In embodiments of the invention a predetermined volume of a sodium phosphate elution buffer is applied to a hydroxyapatite column. In certain embodiments the predetermined volume of sodium phosphate elution buffer is 15-25 column volumes. In a preferred embodiment the predetermined volume of sodium phosphate elution buffer is 20 column volumes.

In another embodiment, the ADC preparation is purified to contain less than 3% aggregates. In a further embodiment, the purified ADC preparation contains less than 1% aggregates.

In an additional embodiment, the ADC preparation contains at least one IgG antibody. More specifically, the ADC preparation contains at least one Notch 3 antibody conjugated to a hydrophobic small molecule drug.

Additional purification method or methods may be used in combination with the hydroxyapatite chromatography of the invention, including, but not limited to affinity chromatography, hydrophobic interaction chromatography, immobilized metal affinity chromatography, size exclusion chromatography, diafiltration, ultrafiltration, anion exchange chromatography, and/or cation exchange chromatography.

In one embodiment of the invention there is provided a method for purifying antibody drug conjugate (ADC) monomers from aggregates in an ADC preparation, the method comprising the steps of: (i) loading an ADC preparation onto a hydroxyapatite resin column, (ii) washing the hydroxyapatite resin column with a low concentration of sodium phosphate buffer; and (iii) eluting the ADC preparation through the column with a gradually increasing concentration sodium phosphate buffer; whereby purified ADC monomers are separated from said aggregates. The concentration of sodium phosphate represented in a gradient of such an embodiment would increase linearly (linear gradient) or non-linearly (non-linear gradient).

Embodiments of the invention (linear gradient method) also include those where the volume of buffer used in step (ii) is about 1-5 column volumes; and preferably about 3 column volumes.

Embodiments of the invention (linear gradient method) also include those where the volume of buffer used in step (iii) is about 5-25 column volumes; and preferably about 20 column volumes.

Embodiments of the invention (linear gradient method) also include those where the concentration of sodium phosphate in step (ii) is about 5 to 35 mM.

Embodiments of the invention (linear gradient method) also include those where the concentration of sodium phosphate in step (iii) gradually increases from about 5 to 35 mM to about 130 to 150 mM.

Further embodiments of the invention (linear gradient method) also include those where concentration of sodium phosphate in step (iii) is initially about 20-25 mM and is gradually increased to about 140 mM.

Further embodiments of the invention (linear gradient method) also include those where the concentration of sodium phosphate in step (iii) is gradually increased to about 130-150 mM over a defined period of time; preferable where the defined period of time is 112-188 minutes; more preferably about 150 minutes.

In another embodiment of the invention there is provided a "step gradient" method for purifying antibody drug conjugate (ADC) monomers from aggregates in an ADC preparation, the method comprising the steps of: (i) loading an ADC preparation onto a hydroxyapatite resin column, (ii) washing the hydroxyapatite resin column with a low concentration of sodium phosphate buffer; and (iii) eluting said ADC preparation through the column with a high concentration of sodium phosphate buffer; whereby purified ADC monomers are separated from said aggregates.

Embodiments of the invention (step gradient method) also include those where the volume of buffer used in step (ii) is about 1-5 column volumes; and preferably about 3 column volumes.

Embodiments of the invention (step gradient method) also include those where the volume of buffer used in step (iii) is about 5-25 column volumes; and preferably about 20 column volumes.

Embodiments of the invention (step gradient method) also include those where the concentration of sodium phosphate in step (ii) is about 5 to 35 mM.

Embodiments of the invention (step gradient method) also include those where the concentration of sodium phosphate in step (iii) is about 80-130 mM.

Embodiments of the invention (step gradient method) also include those where the concentration of sodium phosphate in step (iii) is about 100 mM.

Also provided are embodiments of the invention (linear or step gradient method) where application of the step gradient results in purified ADC contains less than 5% aggregates; less than 3% aggregates; and/or less than 1% aggregates. Additionally, embodiments of the invention include those where purified ADC is at least 95% ADC monomer; purified ADC is at least 97% ADC monomer; and/or purified ADC is at least 99% ADC monomer.

Embodiments of the invention (linear or step gradient method) also include those where the buffer used in step (iii) has a pH from about 6.8 to about 7.5; and preferably a pH of about 7.0 to about 7.3. 39.

Still further embodiments of the invention (linear or step gradient method) also include those where the antibody component of the ADC is an IgG, IgA, IgD, IgE, or IgM antibody; and where the antibody component of the ADC is monoclonal, polyclonal, chimeric, humanized, or a fragment thereof.

Additional embodiments of the invention (linear or step gradient method) also include those where the resin is ceramic hydroxyapatite type I or type II.

Additional embodiments of the invention (linear or step gradient method) also include those where the ADC preparation is first subjecting to ion or anion exchange chromatography.

Embodiments of the invention (linear or step gradient method) include those where the ADC comprises an anti-Notch 3 antibody and an auristatin payload; for instance the anti-Notch 3 ADC of the formula:

where X is an anti-Notch 3 antibody.

Additional embodiments of the invention (linear or step gradient method) also include those where the ADC preparation contains an organic solvent, whereby purified ADC is substantially separated from said solvent. The organic solvent can be dimethyl sulfoxide (DMSO).

Additional embodiments of the invention (linear or step gradient method) also include those where the ADC preparation contains unconjugated payload molecules, whereby purified ADC monomer is substantially separated from said unconjugated payload molecules.

Additional embodiments of the invention (linear or step gradient method) also include those where the purified ADC contains an average DAR of between 3 and 5; and preferably between 3.5 and 4.5.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute part of this specification, and together with the description, serve to explain the principles of the invention.

DETAILED DESCRIPTION

Definitions

In order that the present invention may be more readily understood, certain terms are first defined. Additional definitions are set forth throughout the detailed description.

The term "antibody" (or "Ab") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2) of immunoglobulin. The antibody can be derived from any suitable species. In some embodiments, the antibody is of human or murine origin. An antibody can be, for example, human, humanized or chimeric. Thus the term includes any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. The term "antibody" also includes antibody fragments such as Fab, F(ab')~, Fv, scFv, Fd, dAb, and other antibody fragments that retain antigen-binding function. Typically, such fragments would comprise an antigen-binding domain. Additional definitions of antibodies are found in WO2013/072813 which is hereby incorporated.

"Antibody-drug conjugate" or "ADC" refers to antibodies, or antigen-binding fragments thereof and are conjugated to a drug such as a cytotoxic, cytostatic, and/or therapeutic agent, as described further herein below. For example, a cytotoxic agent can be linked or conjugated to an anti-Notch3 antibody as described herein for targeted local delivery of the cytotoxic agent to tumors (e.g., Notch 3 expressing tumor).

Exemplary anti-Notch3 antibodies include hu28 and hu75, and exemplary anti-Notch3 ADCs include hu28-vc0101, hu75-vc0101, hu28-vc6780 and hu75-vc6780.

The term "column volume" refers to the total volume of the resin bed that is packed in the chromatography column (typically $\pi r^2 h$ where r is the radius of the column and h is the height of the resin bed in the column.

The term "drug" is used herein interchangeably with "payload" and refers to small molecule chemical compound or protein or protein fragment which is conjugated, or to be conjugated, to the antibody. Thus in some embodiments, the drug is a small molecule. In some embodiments, the small molecule is a cytotoxic agent or an imaging agent. In some embodiments, the cytotoxic agent is selected from the group consisting of an anthracycline, an auristatin, a dolastatin, a duocarmycin, an enediyne, a geldanamycin, a maytansine, a puromycin, a taxane, a vinca alkaloid, SN-38, a tubulysin, a hemiasterlin and stereoisomers, isosteres, analogs, or derivatives thereof. In some embodiments, the drug is a biocompatible polymer or a polypeptide. "Drug" as used herein is not to be construed as limited to classical chemical therapeutic agents. For example, the drug moiety may be a protein or polypeptide possessing a desired biological activity.

The term "drug to antibody ratio" (abbreviated as "DAR") refers to the number of drug molecules conjugated per antibody. Compositions, batches, and/or formulations of a plurality of antibody-drug conjugates may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

An "anti-cancer agent" includes, but is not limited to, a drug listed in below: methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel, doxorubicin, epirubicin, 5-fluorouracil, taxanes such as docetaxel and paclitaxel, leucovorin, levamisole, irinotecan, estramustine, etoposide, nitrosoureas such as carmustine and lomustine, L-asparaginase, topotecan, nitrogen mustards, cytoxan, etoposide, BCNU, vinca alkaloids, platinum compounds, mitomycin, gemcitabine, hexamethylmelamine, temsirolimus (CCI-779); lapatinib (GW 572016); RAD-001 (everolimus); XRP-9881; ixabepilone (BMS-247550); pertuzumab (OMNITARG, 2C4); topotecan, tyrosine kinase inhibitors, tyrphostins, imatinib mesylate (GLEEVEC), herbimycin A, genistein, erbstatin, and lavendustin A. In other embodiments, suitable chemotherapeutics include, but are not limited to, alkylating agents: nitrogen mustards (e.g., cyclophosphamide, ifosfamide, trofosfamide, chlorambucil); nitrosoureas (e.g., carmustine (BCNU), lomustine (CCNU)); alkylsulphonates (e.g., busulfan, treosulfan); triazenes (e.g., dacarbazine); Platinum containing compounds (e.g., cisplatin, carboplatin, aroplatin, oxaliplatin); Plant Alkaloids: Vinca alkaloids (e.g., vincristine, vinblastine, vindesine, vinorelbine); Taxoids (e.g., paclitaxel, docetaxel; DNA Topoisomerase Inhibitors: epipodophyllins (e.g., etoposide, teniposide, topotecan, 9-aminocamptothecin, camptothecin, crisnatol); mitomycins (e.g., mitomycin C, antimetabolites); anti-folates: DHFR inhibitors (e.g., methotrexate, trimetrexate) IMP dehydrogenase Inhibitors (e.g., mycophenolic acid, tiazofurin, ribavirin, EICAR); Ribonucleotide reductase Inhibitors (e.g., hydroxyurea, deferoxamine); pyrimidine analogs: uracil analogs (e.g., 5-fluorouracil, floxuridine, doxifluridine, ratitrexed); cytosine analogs (e.g., cytarabine (ara C), cytosine arabinoside, fludarabine); purine analogs (e.g., mercaptopurine, thioguanine); DNA antimetabolites (e.g., 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, pyrazoloimidazole); Hormonal therapies: Receptor antagonists: Anti-estrogen (e.g., tamoxifen, raloxifene, megestrol); aromatase inhibitors (e.g., exemestane, anastrozole, letrozole); GnRH antagonists (e.g., abarelix, histrelin); selective estrogen receptor modulators (SERMs) (e.g., lasofoxifene); LH-RH agonists (e.g., goserelin, tryptorelin, buserelin, leuprolide acetate); Anti-androgens (e.g., flutamide, bicalutamide, nilutamide, megestrol, cyproterone); Retinoids/Deltoids cis-retinoic acid; vitamin A derivative (e.g., all-trans retinoic acid (ATRA-IV)); vitamin D3 analogs (e.g., EB 1089, CB 1093, KH 1060); Photodynamic therapies (e.g., vertoporfin (BPD-MA), phthalocyanine, photosensitizer Pc4, demethoxy-hypocrellin A (2BA-2-DMHA); Angiogenesis Inhibitors: angiostatin (plasminogen fragment), antiangiogenic antithrombin III, 2-methoxyestradiol; Antimitotic agents (e.g., allocolchicine, halichondrin B, colchicine, colchicine derivative, dolstatin 10, maytansine, rhizoxin, thiocolchicine, trityl Cysteine); Other agents: isoprenylation inhibitors; dopaminergic neurotoxins (e.g., 1-methyl-4-phenylpyridinium ion); cell cycle inhibitors (e.g., staurosporine): actinomycins (e.g., actinomycin D, dactinomycin); bleomycins (e.g., bleomycin A2, bleomycin B2, peplomycin); anthracyclines (e.g., daunorubicin, doxorubicin (adriamycin), idarubicin, epirubicin, pirarubicin, zorubicin, mitoxantrone); mTOR inhibitors (e.g., temsirolimus, everolimus); MDR inhibitors (e.g., verapamil); Ca2+ ATPase inhibitors (e.g., thapsigargin); toll-like receptor agonists (e.g., CpG-7909, also known as PF03512676 or PROMUNE; Coley Pharm); costimulatory molecules (e.g., among many other agents known in the art. Additional anti-cancer agents that may be used in the methods of the present invention include, but are not limited to: acivicin; aclarubicin; acodazole hydrochloride; acronine; adozelesin; aldesleukin; altretamine; ambomycin; ametantrone acetate; amifostine trihydrate; aminoglutethimide; amsacrine; anastrozole; anthramycin; azacitidine; azetepa; azotomycin; bisantrene hydrochloride; bisnafide dimesylate; bizelesin; bleomycin sulfate; bortezomib; brequinar sodium; bropirimine; busulfan; cactinomycin; calusterone; capecitabine; caracemide; carbetimer; carboplatin; carmustine; carubicin hydrochloride; carzelesin; cedefingol; chlorambucil; cirolemycin; cisplatin; chlorambucil; cladribine; clodronate; crisnatol mesylate; cyclophosphamide; cytarabine; dacarbazine; dactinomycin; darbepoietin; daunorubicin hydrochloride; decitabine; dexormaplatin; dexrazoxane; dezaguanine; dezaguanine mesylate; diaziquone; diethylstilbestrol; docetaxel; doxorubicin; doxorubicin hydrochloride; droloxifene; droloxifene citrate; dromostanolone propionate; duazomycin; farmorubicin; edatrexate; eflornithine hydrochloride; elsamitrucin; enloplatin; enpromate; epipropidine; epirubicin hydrochloride; erbulozole; erlotinib; erythropoietin; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgastrim (G-CSF); floxuridine; fludarabine phosphate; fludrocortisone; fluorouracil; fluoxymesterone; flurocitabine; fosquidone; fostriecin sodium; fulvestrant; gefitinib; gemcitabine; gemcitabine hydrochloride; gemtuzumab; goserelin; imatinib; irinotecan hydrochloride; ixabepilone; ketoconazole; lanreotide acetate; lapatinib; letrozole; leucovorin; leuprolide acetate; levamisole; liarozole hydrochloride; lometrexol sodium; lomustine; losoxantrone hydrochloride; masoprocol; maytansine; mechlorethamine hydrochloride; medroxyprogesterone; megestrol acetate; melengestrol acetate; melphalan; menogaril; mercaptopurine; mesna; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; octreotide; ormaplatin; oxaliplatin; oxisuran; paclitaxel; pamidronate; peliomycin; pentamustine; pentostatin; peplomycin sulfate; perfosfamide; pipobroman; piposulfan; piroxantrone hydrochloride; plicamycin; plomestane; porfimer sodium; porfimer; porfiromycin; prednimustine; pemetrexed; procarbazine hydrochloride; puromycin; puromycin hydrochloride; pyrazofurin; raltitrexed; riboprine; rituximab; rogletimide; safingol; safingol hydrochloride; semustine; simtrazene; spiromustine; spiroplatin; streptonigrin; streptozocin; sulofenur; sunitinib; streptozocin; talisomycin; tecogalan sodium; tegafur; teloxantrone hydrochloride; temoporfin; temozolomide; temsirolimus; teniposide; teroxirone; testolactone; thalidomide; thiamiprine; thioguanine; thiotepa; tiazofurin; tirapazamine; topotecan; toremifene citrate; trastuzumab; tretinoin; trestolone acetate; triciribine phosphate; trimetrexate; trimetrexate glucuronate; triptorelin; topotecan; tubulozole hydrochloride; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zolendronate; zorubicin hydrochloride. Other anti-cancer drugs that can be used include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin;

gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The term "antibody drug conjugate preparation" refers to any composition containing an ADC and potentially unwanted impurities, for instance high molecular weight species such as aggregates, solvents, free residual drug and related species, and other species resulting or remaining from the conjugation process.

"Ceramic hydroxyapatite" or "cHA" refers to an insoluble hydroxylated calcium phosphate of the formula [Capp(PO4)p(OH)~], which has been sintered at high temperatures into a spherical, macroporous ceramic form. The term "cHA" encompasses, but is not limited to, Type I and Type II ceramic hydroxyapatite. Unless specified, "cHA" refers to any particle size including, but not limited to, 20, 40, and 80 μm.

The term "high molecular weight species" or "HMWS" refers to any high molecular weight impurity, but typically an aggregate. (High molecular weight species are sometimes referred to as high molecular mass species, or HMMS, in the scientific literature.)

An "aggregate" is an association of at least two or more components selected from unconjugated antibodies and ADC monomers (e.g., dimers comprising two ADC monomers, dimers comprising an unconjugated antibody and an ADC monomer, trimers comprising various combinations of ADC monomers and unconjugated antibodies, and the like) An aggregate may arise by any method including, but not limited to, covalent, non-covalent, disulfide, or non-reducible crosslinking. The antibody portion of the aggregate components may each be in the form of a complete antibody, an antibody fragment, or other forms described in the definition of "antibody" above.

The term "vc" or "vc linker" refers to maleimidocapronic-valine-citruline-p-aminobenzyloxycarbonyl, also known as "mcValCitPABC-" or "MalCValCitPABC-", having the following structure:

The term "0101" or "0101 payload" refers to (2-methyl-alanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), having the following structure:

The term "6780" or "6780 payload" refers to (2-methyl-alanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide), having the following structure:

The term "vc0101" or "vc0101 linker-payload" refers to a linker-payload having the formula:

The term "vc6780" or "vc6780 linker-payload" refers to a linker-payload having the formula:

Description of the Method

The present invention provides methods for removing high molecular weight species, specifically aggregates, from antibody drug conjugate (ADC) preparations using hydroxyapatite chromatography and a phosphate gradient elution. The present invention is useful for large scale purification of antibody drug conjugate preparations. The method uses a hydroxyapatite support charged with phosphate at neutral pH and low ionic strength to bind both the antibody drug conjugate monomers and the corresponding aggregates. The column is then washed with a phosphate buffer to remove loosely bound impurities such as solvent and residual small molecule compounds. Next, the ADC is selectively eluted using a phosphate buffer of increasing strength under gradient conditions containing, in certain embodiments, from about 5-35 mM to about 130-150 mM (preferably 140 mM) sodium phosphate at slightly acidic to slightly basic pH. The aggregates are separated from the ADC monomers in these gradient conditions. The resin is optionally regenerated using sodium or potassium phosphate buffer solution of higher ionic strength. The resin is optionally washed with aqueous sodium hydroxide solution.

In one embodiment of the invention, the purified ADC preparation contains less than 3% aggregates, and in another embodiment less than 1% aggregates.

The present invention further provides ADC monomers that have an optimized average DAR and narrow DAR distribution. The average DAR and DAR distribution can have an effect on the clinical efficacy of an ADC, in particular, an effect on both potency and potential toxicity of the ADC, and can have a significant effect on properties, such as stability and aggregation of the ADC.

The DAR distribution provides the percent or fraction of various ADC monomer species, e.g. DAR 0 to 8, that may be present in a composition, batch, and/or formulation of ADCs. The DAR distribution of a composition, batch, and/or formulation of ADCs may be determined by methods known in the art, such as UV, hydrophobic Interaction chromatography (HIC), capillary iso-electric focusing (cIEF) or reduced reverse phase chromatography (RP-HPLC). The DAR distribution of a composition, batch, and/or formulation of ADCs may be characterized as a highly heterogeneous mixture with a broad DAR distribution, generally containing a broad range of ADC monomer species with DAR 0 to 8. The DAR distribution of a composition, batch, and/or formulation of ADCs may be characterized as a highly homogeneous mixture with a narrow DAR distribution, generally containing a narrow range of ADC monomer species having a particular DAR, such as DAR 3 to 5.

In particular aspects of the present invention, the improved conjugation and purification conditions disclosed herein provide anti-Notch 3 ADCs with an optimized average DAR in the range of about 3 to 5, preferably about 4, and a narrow DAR distribution, for example less heterogeneity, in monomer species with a DAR from 3 to 5 (which are the most desired).

In particular aspects of the invention, it is beneficial to eliminate ADCs having a high DAR (DAR>6) which are more hydrophobic and demonstrate faster clearance, which may contribute to higher toxicity and lower the therapeutic index (TI). In other aspects of the invention, it is beneficial to eliminate ADCs having a low DAR (DAR<2) which contribute little to efficacy, however, provide an increase in the amounts of unconjugated antibody which may compete with the ADC for the target antigen, such as Notch 3, and lead to a lower TI. In another aspect of the invention, it is beneficial to eliminate ADCs having a high DAR (DAR>6) and ADCs having a low DAR (DAR<2).

In one embodiment of the invention the purified ADC contains drug loading (drug to antibody ratio, DAR) between 3.5 and 4.5 and in another embodiment between 3 and 5.

The Hydroxyapatite Resin

Various hydroxyapatite chromatographic resins are available commercially, and any available form of the material can be used in the practice of this invention. In one embodiment of the invention, the hydroxyapatite is in a crystalline form. Hydroxyapatites for use in this invention may be those that are agglomerated to form particles and sintered at high temperatures into a stable porous ceramic mass. The particle size of the hydroxyapatite may vary widely, but a typical particle size ranges from 1 µm to 1,000 µm in diameter, and may be from 10 µm to 100 µm. In one embodiment of the invention, the particle size is 20 µm. In another embodiment of the invention, the particle size is 40 µm. In yet another embodiment of the invention, the particle size is 80 µm. A number of chromatographic supports may be employed in the preparation of cHA columns; the most extensively used are Type I and Type II hydroxyapatite. Type I has a high protein binding capacity and better capacity for acidic proteins. The choice of a particular hydroxyapatite type can be determined by the skilled practitioner.

This invention may be used with hydroxyapatite resin that is loose, packed in a column, or in a continuous annual chromatograph. In one embodiment of the invention, ceramic hydroxyapatite resin is packed in a column. The choice of column dimensions can be determined by the skilled artisan. In one embodiment of the invention, a column diameter of at least 1 cm with a bed height of about 22 cm may be used for small scale purification. In an additional embodiment of the invention, a column diameter of from about 7 cm to about 30 cm may be used. In certain embodiments of the invention, a slurry of ceramic hydroxyapatite resin in up to 200 mM sodium phosphate solution at pH 7.0 may be used to pack the column at a constant flow rate of about 4 cm/min or with gravity.

Hydroxyapatite resins of the type useful in this invention may be obtained from Bio-Rad.

Buffer Compositions and Loading Conditions

Before contacting the hydroxyapatite resin with the ADC preparation, it may be necessary to adjust parameters such as pH, ionic strength, and temperature and in some instances the addition of substances of different kinds. Thus, it is an optional step to perform an equilibration of the hydroxyapatite matrix by washing it with a solution (e.g., a buffer for adjusting pH, ionic strength, etc., or for the introduction of a detergent) bringing the necessary characteristics for purification of the antibody preparation. In combination binding/elution mode hydroxyapatite chromatography, the hydroxyapatite matrix is equilibrated and washed with a solution. In one embodiment of the invention, the matrix may be equilibrated using a solution containing from 5 mM to 500 mM sodium phosphate at slightly basic to slightly acidic pH. For example, the equilibration buffer may contain 10 to 500 mM sodium phosphate, in another embodiment it may contain 5 to 10 mM sodium phosphate, in another embodiment it may contain 2 to 5 mM sodium phosphate, in another embodiment it may contain 2 mM sodium phosphate, and in another embodiment may contain 5 mM sodium phosphate. The pH of the load buffer may range from 6.8 to 8.0. In one embodiment, the pH may be from 7.0 to 7.3, and in another embodiment the pH may be 7.5. The ADC preparation may also be buffer exchanged into an appropriate buffer or load buffer in preparation for hydroxyapatite chromatography. For example, the load buffer may contain 2 mM to 10 mM sodium phosphate, in another embodiment it may contain 2 to 8 mM sodium phosphate, in another embodiment it may contain 3 to 7 mM sodium phosphate, and in another embodiment may contain 5 mM sodium phosphate. In one embodiment, the pH may be from 6.8 to 8.0, and in another embodiment the pH may be 7.0.

The contacting of an ADC preparation to the hydroxyapatite resin may be performed in a packed bed column, a fluidized/expanded bed column containing the solid phase matrix, and/or in a simple batch operation where the solid phase matrix is mixed with the solution for a certain time.

After contacting the hydroxyapatite resin with the antibody drug conjugate preparation there is optionally performed a washing procedure. The washing buffers employed will depend on the nature of the hydroxyapatite resin, the mode of hydroxyapatite chromatography being employed, and therefore can be determined by one of ordinary skill in the art. During the washing operation any solvent and other small molecule impurities such as unconjugated free drug can be and typically are removed from the ADC mixture. Washing typically comprises the use of 1-5 column volumes, preferably about 3 column volumes, of a washing buffer as described herein. In a bind and elute mode, the ADC may be eluted from the column after a washing procedure. For elution of the ADC from the column, this invention uses a higher ionic strength phosphate buffer containing up to 200 mM at slightly acidic or slightly basic pH. In another embodiment it may contain about 15 to 150 mM sodium phosphate; in another embodiment it may contain about 20 mM to 150 mM sodium phosphate.

In one embodiment, the pH may be from 6.8 to 7.3, in another embodiment the pH may be 7.0, in another embodiment the pH may be 7.5 and in another embodiment the pH may be 8.0. The elution buffer may be altered for elution of the ADC from the column in a continuous or stepwise gradient.

The hydroxyapatite resin may optionally be cleaned, i.e. stripped and regenerated, after elution of the ADC. This procedure is typically performed regularly to minimize the building up of impurities on the surface of the solid phase and/or to sterilize the matrix to avoid contamination of the product with microorganisms.

Buffer components may be adjusted according to the knowledge of the person of ordinary skill in the art. Sample buffer composition ranges and examples for binding mode elution are provided in Tables 1 and 2. Not all of the buffers or steps are necessary, but are provided for illustration only. For example, it may not be necessary to have two distinct equilibration steps, and it may not be necessary to strip, regenerate, or store the hydroxyapatite resin.

Although it has been discovered that hydroxyapatite chromatography can be used alone to separate monomeric ADC species from aggregates, as mentioned above, the purification method of the invention can be used in combination with other protein purification techniques. In one embodiment of the invention, one or more steps preceding the hydroxyapatite step may be desirable to reduce the load challenge of the contaminants or impurities. In another embodiment of the invention, one or more purification steps following the hydroxyapatite step may be desirable to remove additional contaminants or impurities.

The hydroxyapatite chromatographic (cHA) purification procedure described may optionally be combined with other purification steps, including but not limited to, Protein A chromatography, affinity chromatography, hydrophobic interaction chromatography, immobilized metal affinity chromatography, size exclusion chromatography, diafiltration, ultrafiltration, ion exchange chromatography.

Removal of Additional Impurities

In addition aggregate removal, cHA chromatography has been shown useful in removing other impurities from the ADC preparations. Other impurities that may be removed by the cHA chromatography methods of the invention include, but are not limited to organic solvents, small molecule free drugs (unconjugated payloads or any species that originating from the payloads), reagents used for quenching the reaction mixture, reagents used for reduction of an antibody and any small molecule byproducts originating from the reducing agent, protein contaminants from prior purification steps, and solvents that are used for the preparation of the ADC mixture.

In one embodiment of the invention, the invention is able to remove organic solvent dimethyl sulfoxide (DMSO) from the ADC preparation from 11% to less than the limit of detection by analytical techniques.

In another embodiment of this invention, the invention is able to remove small molecule toxic payload from the ADC preparation from approximately 0.2 mg/mL to less than the limit of detection by analytical techniques.

The organic solvents and small molecules impurities such as payload do not bind to the hydroxyapatite resin under elution conditions of this invention. These impurities elute early in the wash portion (Table 1) of the purification after the column loading (see FIG. 1). This enables easy separation of these impurities from the ADC molecules.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

EXAMPLES

Tables Showing Representative Purification Parameters

TABLE 1

Buffer Compositions Using a Linear Gradient in the Mobile Phase

| Step | Buffer Composition | Column Volume | Flow rate cm/h |
|---|---|---|---|
| Wash | Water (if column is stored in 0.1N NaOH) | 1 | 240 |
| Equilibration 1 | 500 mM sodium phosphate, pH 7.0 | 2 | 240 |
| Equilibration 2 | 10% Buffer B | 5 | 240 |
| Sample Adjustment | use buffer C to add phosphate to the loading material to bring phosphate content to 10 mM in the loading solution | | |
| Loading | 15 g of loading sample/L of resin | | 180 |
| Wash | 10% buffer B | 3 | 180 |
| Elution | 10%-70% buffer B | 20 | 180 |
| Stripping and Regeneration | Buffer C | 3 | 180 |
| Storage | 100 mM NaOH | 4 | 180 |

Buffer A: 5 mM Sodium Phosphate, pH 7.0,
Buffer B: 200 mM Sodium Phosphate, pH 7.0,
Buffer C: 500 mM sodium phosphate, pH 7.0

TABLE 2

Buffer Compositions Using a Step Gradient of the Mobile Phase

| Step | Buffer Composition | Column Volume | Flow rate, cm/h |
|---|---|---|---|
| Wash | Water (if column is stored in 0.1N NaOH) | 1 | 240 |
| Equilibration 1 | Buffer C | 2 | 240 |
| Equilibration 2 | 10% Buffer B | 5 | 240 |
| Sample Adjustment | Use buffer C to add phosphate to the loading material to bring phosphate content to 10 mM in the loading solution | | |
| Loading | 15 g of loading sample/L of resin | | 180 |
| Wash | 10% buffer B | 3 | 180 |
| Elution | 50% buffer B | 10 | 180 |
| Stripping and Regeneration | Buffer C | 3 | 180 |
| Storage | 100 mM NaOH | 4 | 180 |

Buffer A: 5 mM Sodium Phosphate, pH 7.0,
Buffer B: 200 mM Sodium Phosphate, pH 7.0,
Buffer C: 500 mM sodium phosphate, pH 7.0

The conditions described in Tables 1 and 2 are employed in some of the following representative Examples.

Example 1: Conjugation and Purification of Notch 3 Antibody to Vc0101 Linker-Payload Conjugation of ADC: The pH of a stock solution of anti-Notch 3 antibody was adjusted to 6.5-7. The solution of antibody was warmed to 37° C. An aqueous solution of TCEP (tris(2-carboxyethyl)phosphine, 2.2 equiv.) was added to the antibody solution. The resulting solution was stirred for 90 minutes at 37° C. The solution was then cooled to ambient temperature. To this antibody solution was added a solution of excess of vc0101 in DMSO. The reaction mixture was stirred for 1 hour. The mixture was quenched by addition of L-cysteine. The reaction mixture was filtered through 0.22 μm filter. The resulting approximately 50 grams of unpurified product consisted of an ADC with average drug to antibody ratio (DAR)~4.2 as evaluated by hydrophobic interaction chromatography (HIC) and aggregate levels ~5%, as evaluated by size exclusion chromatography (SEC).

Analysis of Crude ADC Preparation: The analytical HIC method was used to determine drug loading and drug load distribution of the ADC. The reference material and test samples were diluted and injected onto a HIC column. Species of different drug to antibody ratio (DAR) were separated using a salt gradient and detected by UV absorbance at 280 nm. The average DAR and distribution profile were determined by peak area percentage of each species. The SEC method was used to determine product purity and aggregate content. The test samples were diluted and injected onto a size-exclusion column. The aggregate and monomer species in the crude ADC preparation were reported as the percent of the total area for all protein-related peaks.

Preparation of Hydroxyapatite Column: A 7.5 mL hydroxyapatite resin (type I, 40 μm) column was washed with 1 column volume (CV) water, then equilibrated with 2 CV of 500 nM sodium phosphate at pH 7.0 and then 5 CV of 10% Buffer B. The column was the adjusted with Buffer C to bring the phosphate content to 10 mM). 15 g of the crude ADC preparation was added to the column and washed with 3 CV of 10% Buffer B. (Buffers compositions and column conditions are as defined in Table 1, above.)

Figure 1:
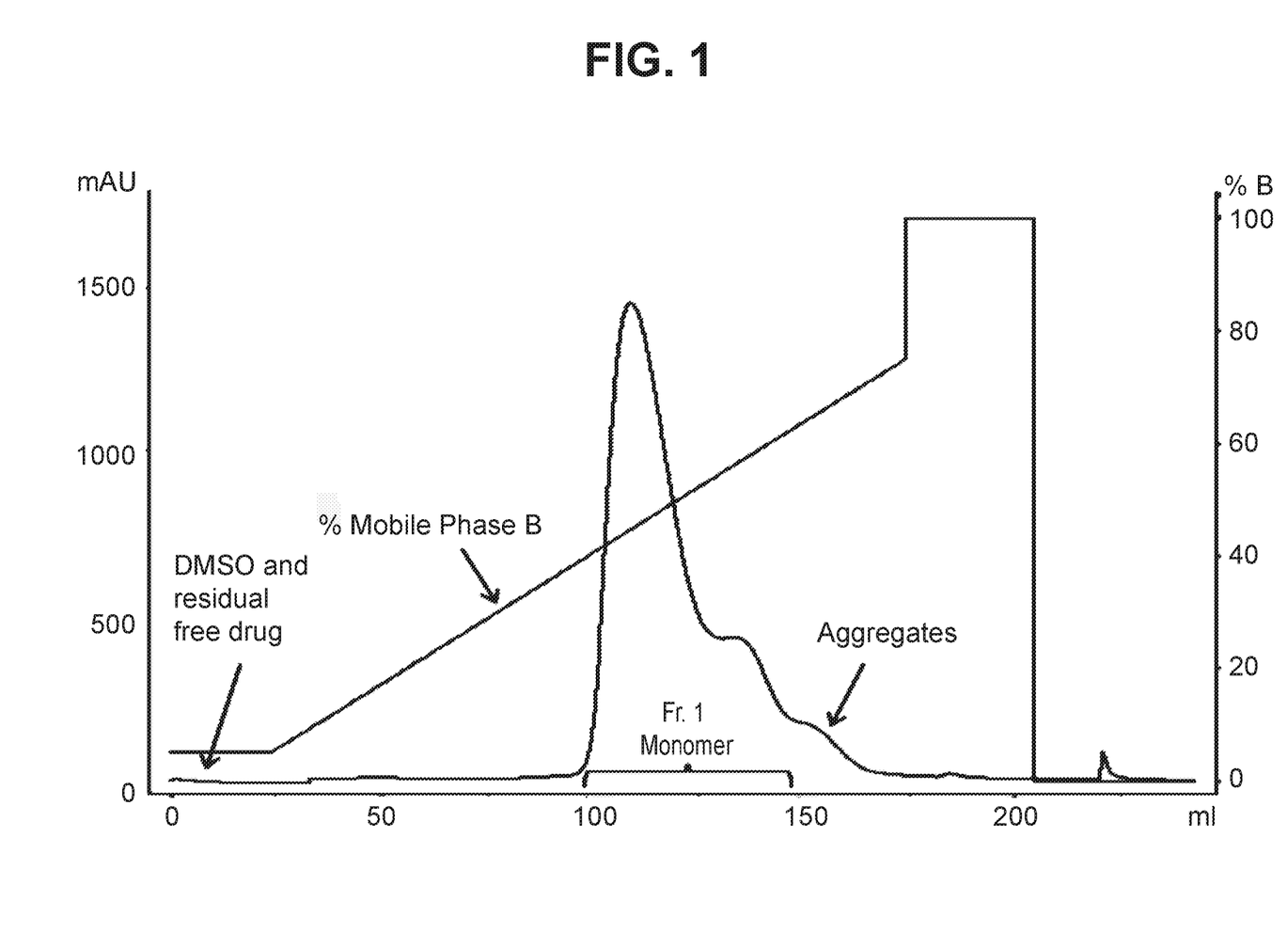
FIG. 1 shows the separation of aggregates using a phosphate gradient on a hydroxyapatite resin column.

Purification of the Conjugation Mixture Using Column Chromatography: Consistent with Table 1 parameters, the following column purification conditions were used: Mobile phase A: 5 mM sodium phosphate, pH 7; Mobile phase B: 200 mM sodium phosphate, pH 7; buffer gradient=10-70% mobile phase B over 20 CV, protein loading=15 mg/mL, flow rate=1 mL/min, column bed height=22 cm, CV=7.5 mL. The purification profile is shown in FIG. 1.

Most of the desired monomer product eluted between beginning of the peak (~50 mAU absorbance) through the next 6.9 column volumes in fraction 1 (Fr.1). Four main fractions were collected. The first fraction was collected from beginning of the product peak through the next 6.9 CV, followed by fractionation at every ⅓ CV for the next three fractions. The fractions were analyzed by in-process UV assay for values of drug-antibody ratio (DAR) and by SEC analytical method for aggregates. Most of the monomer eluted in fraction 1 of the collected set of fractions affording ADC product in 85-88% yield (based on the protein yield), DAR=3.6 containing level of aggregates ~1%. The aggregates were in the last peak as shown in the chromatogram.

Ultrafiltration-Diafiltration (UF-DF): The ADC material obtained after column purification was further purified with the ultrafiltration/diafiltration process (UF-DF) using Ultracel membrane cartridges (30 kD) and 20 mM histidine buffer as diafiltration buffer (pH 5.8). The retentate solution was collected and filtered through 0.22 μm filter.

Example 2: Purification of Notch 3 ADC on Hydroxyapatite Resin with the Mobile Phase Buffer pH of 7.5

Figure 2:
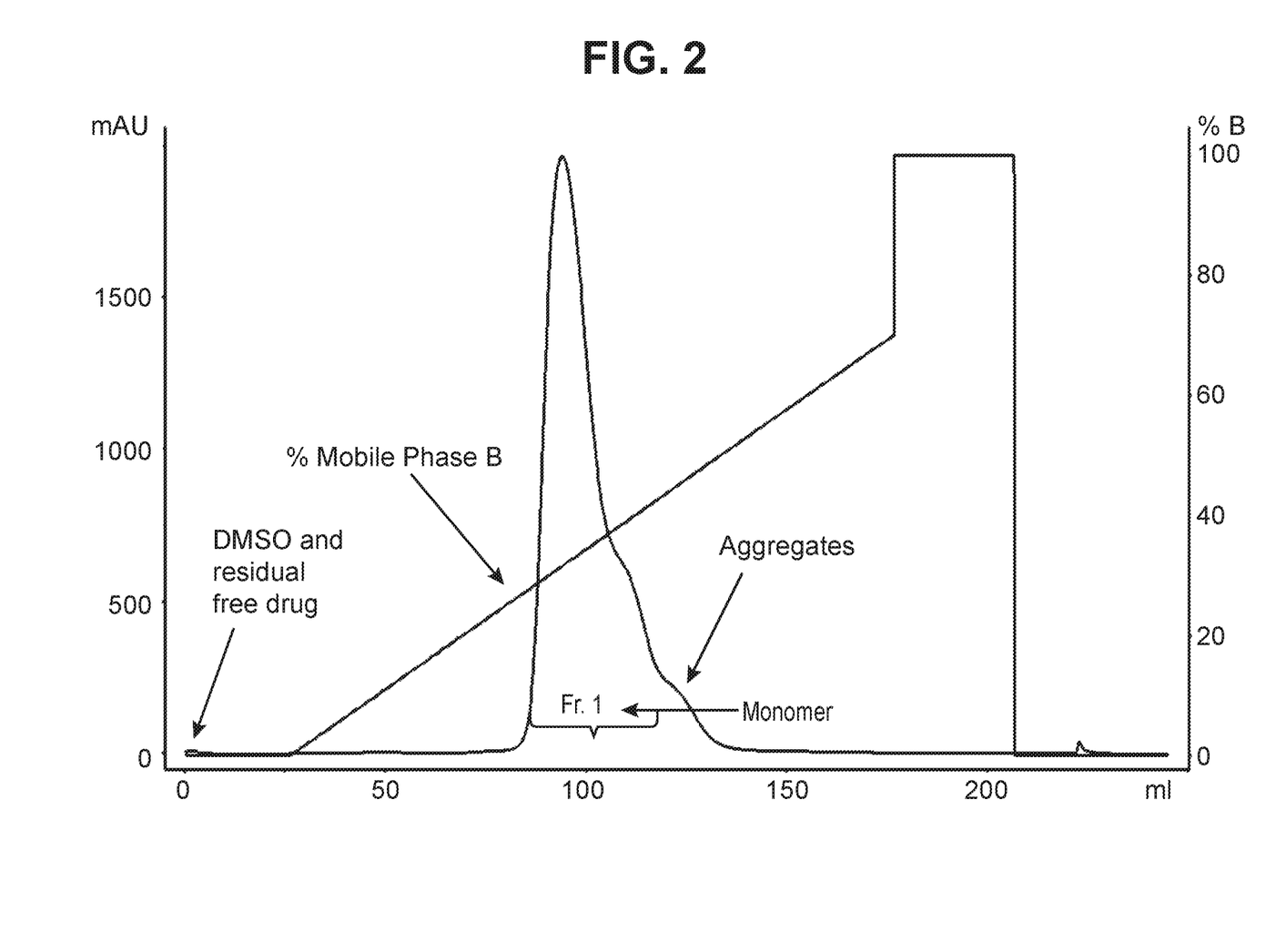
FIG. 2 shows the separation of aggregates using a phosphate gradient on a hydroxyapatite resin column at pH 7.5.

Following ADC conjugation procedures and column preparation procedures substantially as described in Example 1 and Table 1 above (except with respect to buffer pH), the conjugation product containing aggregates ~4.5% and DAR ~4 as determined by analytical SEC method was purified on hydroxyapatite resin using the phosphate buffer having a pH 7.5. The purification conditions were as follows, Mobile phase A: 5 mM sodium phosphate, pH 7.5, Mobile phase B: 200 mM sodium phosphate, pH 7.5, mobile phase gradient=10-70% B over 20 column volumes, protein loading=15 mg/mL, flow rate=1 mL/min, bed height=22 cm, column volume=7.5 mL Fraction 1 was collected from the beginning of the peak to 5 column volumes. This fraction contained most of the monomer as determined by analytical SEC method. Later fractions contained primarily aggregates. The resulting ADC product in fraction 1 was obtained with aggregate content of 1.5% and DAR of 4 as determined by SEC. The ADC yield from the column step was 88%. The purification chromatogram is shown in FIG. 2.

Examples 3 Through 13: Evaluation of Purification of Notch 3 ADC on Hydroxyapatite Resin at Various Flow Rates and Phosphate Gradients Examples 4 through 14 demonstrate purification protocols similar to those described above in Examples 1 and 2. Except for these parameters, all other parameters used for these purification examples are from Table 1. The varied experimental parameters for Examples 3 through 13 are provided in Table 3. These conjugation products contained, generally, about 4.5% aggregates and DAR of about 4 as determined by analytical HIC method. Purification occurred on hydroxyapatite resin using phosphate buffer gradients listed. Process control data and quality results from these evaluations are also listed in the Table 3. The following experiment conditions were used for purification evaluation: Mobile phase A: 5 mM sodium phosphate, pH 7; Mobile phase B: 200 mM sodium phosphate, pH 7; Gradient=as listed under parameters in the table over 20 column volumes, Protein loading=15 mg/mL, Flow rate=1 mL/min, Bed height=22 cm

TABLE 3

Additional Purification Protocols

| | Parameters | | | Process Results and Quality attributes | | | |
|---|---|---|---|---|---|---|---|
| Example | Flow rate | Start % B | End % B | Conductivity at 50 mAU at beginning of peak (μS/cm) | Conductivity at second inflection point at the peak tail (μS/cm) | % aggregates of Fr 1 (at 7 CV) | DAR |
| 3 | 0.85 | 5 | 65 | 8.8 | 13.1 | 0.7 | 3.8 |
| 4 | 0.85 | 10 | 70 | 8.9 | 13.2 | 0.7 | 3.8 |
| 5 | 0.85 | 15 | 75 | 8.9 | 13.2 | 0.6 | 3.8 |
| 6 | 1.00 | 5 | 70 | 8.8 | 13.3 | 0.9 | 3.8 |
| 7 | 1.00 | 10 | 75 | 9.1 | 13.8 | 4.4 | 4.0 |
| 8 | 1.00 | 15 | 65 | 8.6 | 12.8 | 0.4 | 3.8 |
| 9 | 1.15 | 5 | 75 | 8.8 | 13.5 | 3.4 | 4.0 |
| 10 | 1.15 | 10 | 65 | 8.7 | 13.0 | 0.6 | 3.9 |
| 11 | 1.15 | 15 | 70 | 8.6 | 13.1 | 1.8 | 3.9 |
| 12 | 1.00 | 10 | 70 | 8.8 | 13.2 | 0.9 | 3.9 |
| 13 | 1.00 | 10 | 70 | 8.8 | 13.2 | 1.2 | 3.9 |

Example 14: Evaluation of Step Gradient for Purification of Notch 3 ADC on a Hydroxyapatite Resin Column A conjugation product containing aggregates ~4.5% and DAR ~4 as determined by analytical HIC method was purified on hydroxyapatite resin using step gradient of the phosphate buffer. The purification conditions from Table 2 were used for the purification process: Mobile phase A: 5 mM sodium phosphate, pH 7; Mobile phase B: 200 mM sodium phosphate, pH 7; Protein loading=15 mg/mL, Flow rate=1 mL/min, bed height=22 cm, and other conditions consistent with Table 2, above. Two purification conditions using step gradient were evaluated as shown in Table 4. The results on the level of aggregates and drug-antibody ratio are also listed in Table 4.

TABLE 4

Evaluation of step gradient for purification of Notch 3 ADC on hydroxyapatite resin

| Run | Step Gradient Conditions | Fractions Collected | Aggregates (%) by SEC | DAR (HIC) |
|---|---|---|---|---|
| 1 | Wash 3 CV(10% B) then 50% B for 10 CV | 2 CV after start of peak elution | 2.6 | Not evaluated due to higher than expected aggregates |
| 2 | Wash 3 CV(10% B) then 45% B for 10 CV | 3 CV after start of peak elution | 1.3 | 3.9 |

Figure 3:
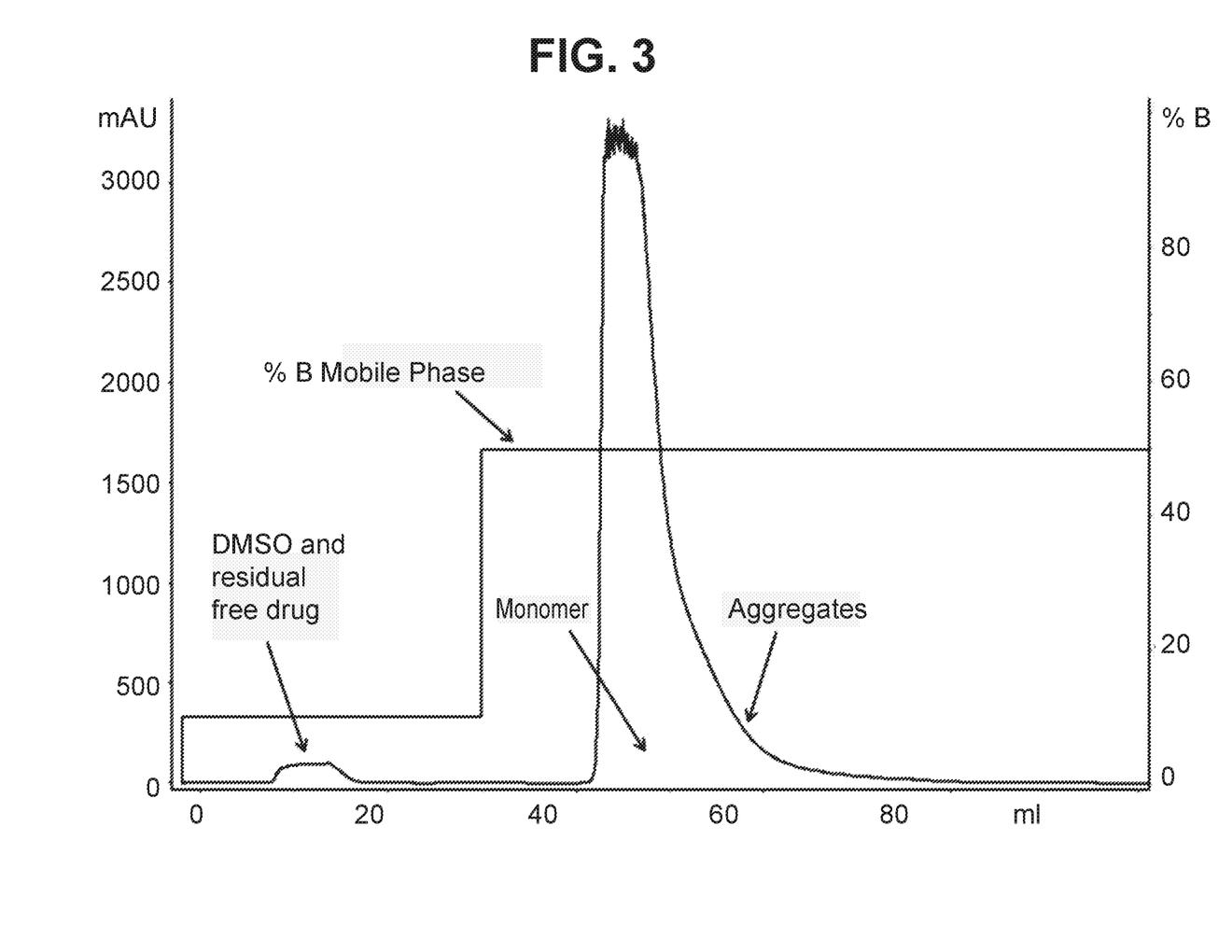
FIG. 3 shows the purification of a Notch 3 ADC on a hydroxyapatite resin using a step gradient.
Figure 4:
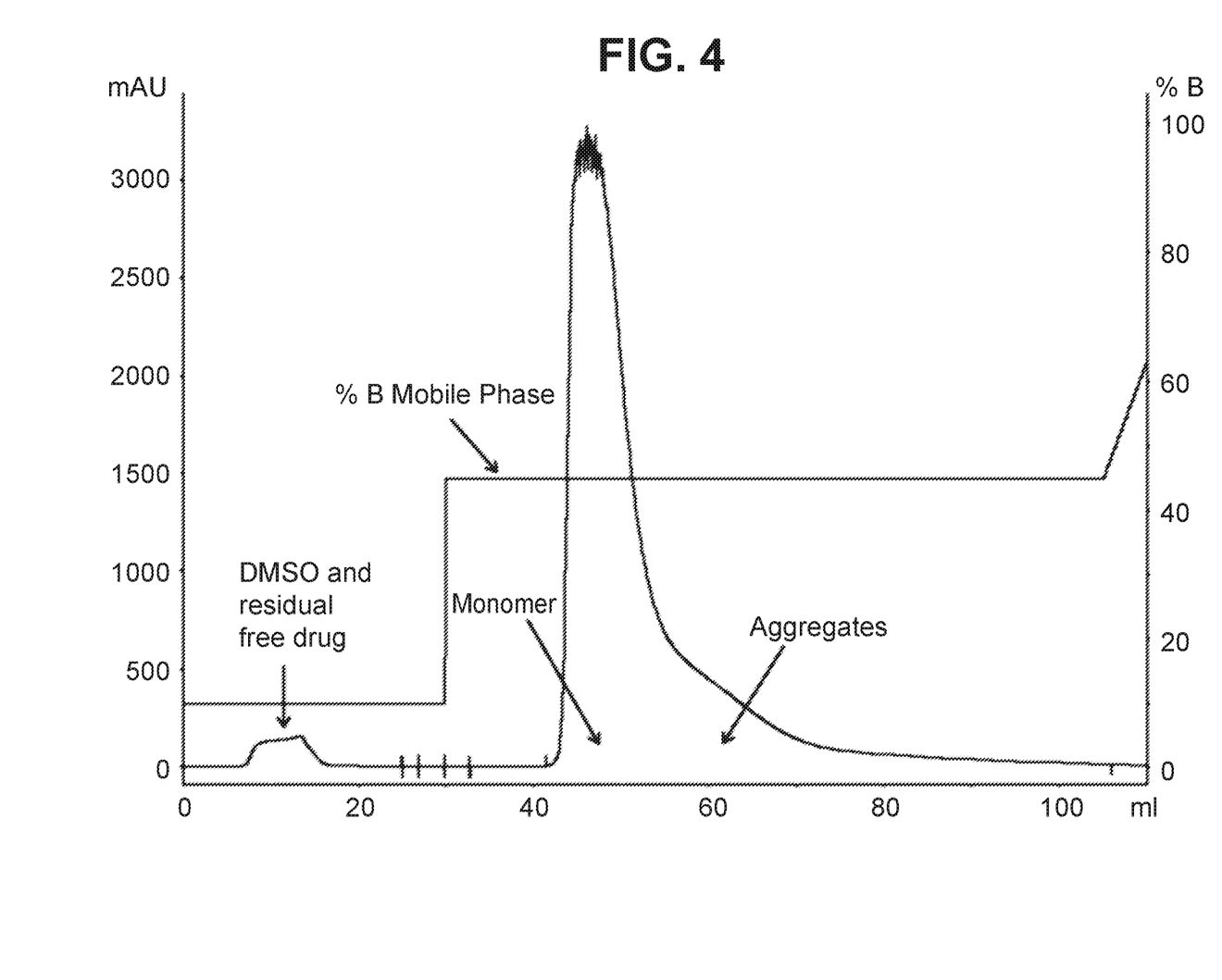
FIG. 4 shows the purification of a Notch 3 ADC on a hydroxyapatite resin using a step gradient.

The chromatography profiles of the step gradient are shown in FIG. 3 (Run 1) and FIG. 4 (Run 2).

Figure 5:
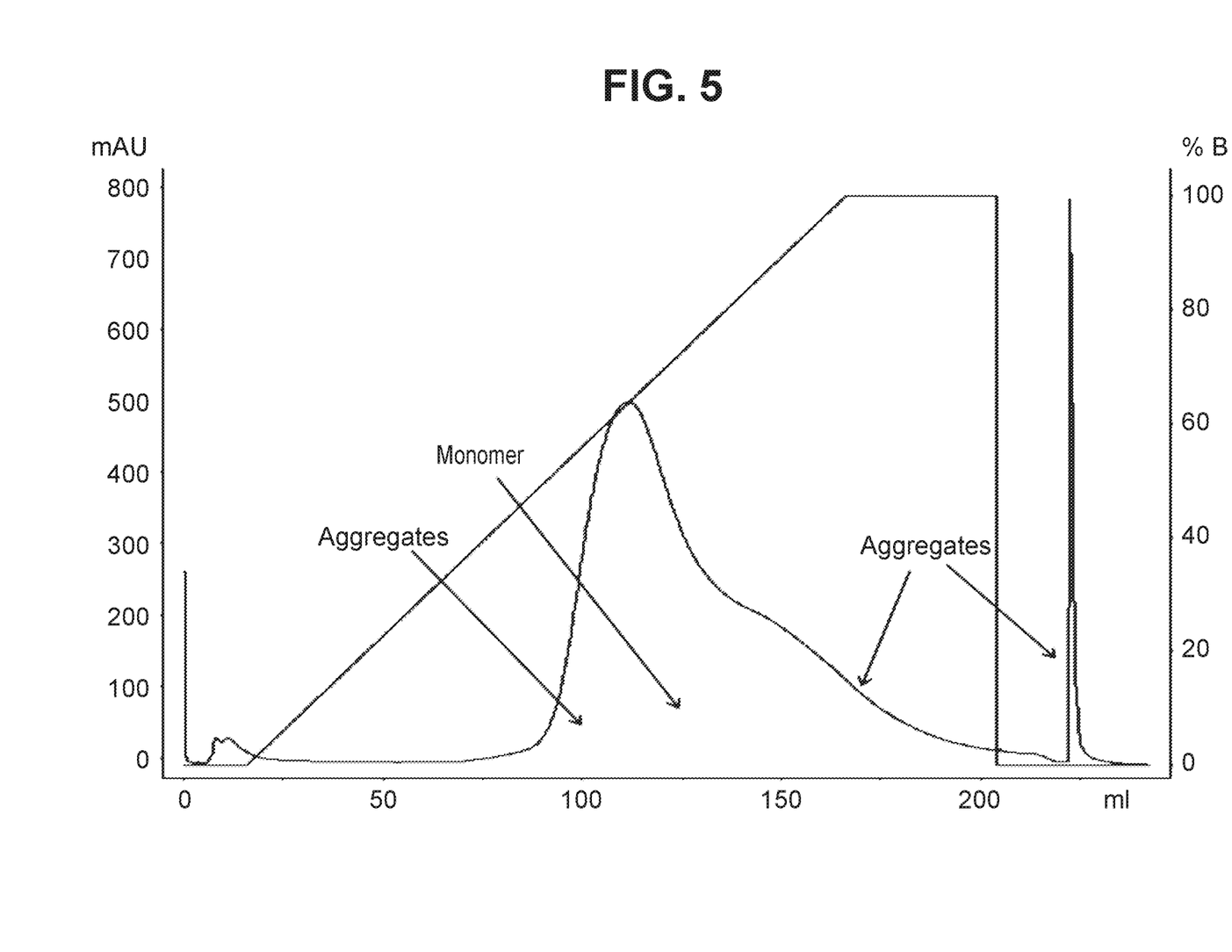
FIG. 5 shows the purification of a Notch 3 ADC on a hydroxyapatite resin using a mobile phase containing a low concentration of sodium chloride.

Example 15: Purification of Notch 3 ADC on Hydroxyapatite Resin Using Mobile Phase Containing Low Concentration of Sodium Chloride The conjugation product containing aggregates ~4.5% and DAR ~4 as determined by SEC and analytical HIC was purified on hydroxyapatite resin using phosphate/sodium chloride/HEPES buffers. Following conditions were used for the purification process: Mobile phase A: 5 mM sodium phosphate, 20 mM HEPES buffer, pH 7; Mobile phase B: 5 mM sodium phosphate, 20 mM HEPES, 0.5 M sodium chloride, pH 7; Protein loading=13 mg/mL, Flow rate=1 mL/min, bed height=22 cm, Gradient=0-100% B over 20 column volumes. Several fractions were collected and analyzed by SEC assay for presence of aggregates and by UV assay for the DAR. The early and late eluting fractions contained most of the aggregates. Fractions containing lower aggregate levels were pooled and evaluated for aggregate and DAR content. The aggregate content of the product pool was 3.3% and the DAR value was purified ADC was 3.9. The ADC product was obtained in 86% yield. Only moderate reduction of ~1% in the aggregate levels was observed compared to the unpurified product. The purification chromatogram is shown in FIG. 5.

Figure 6:
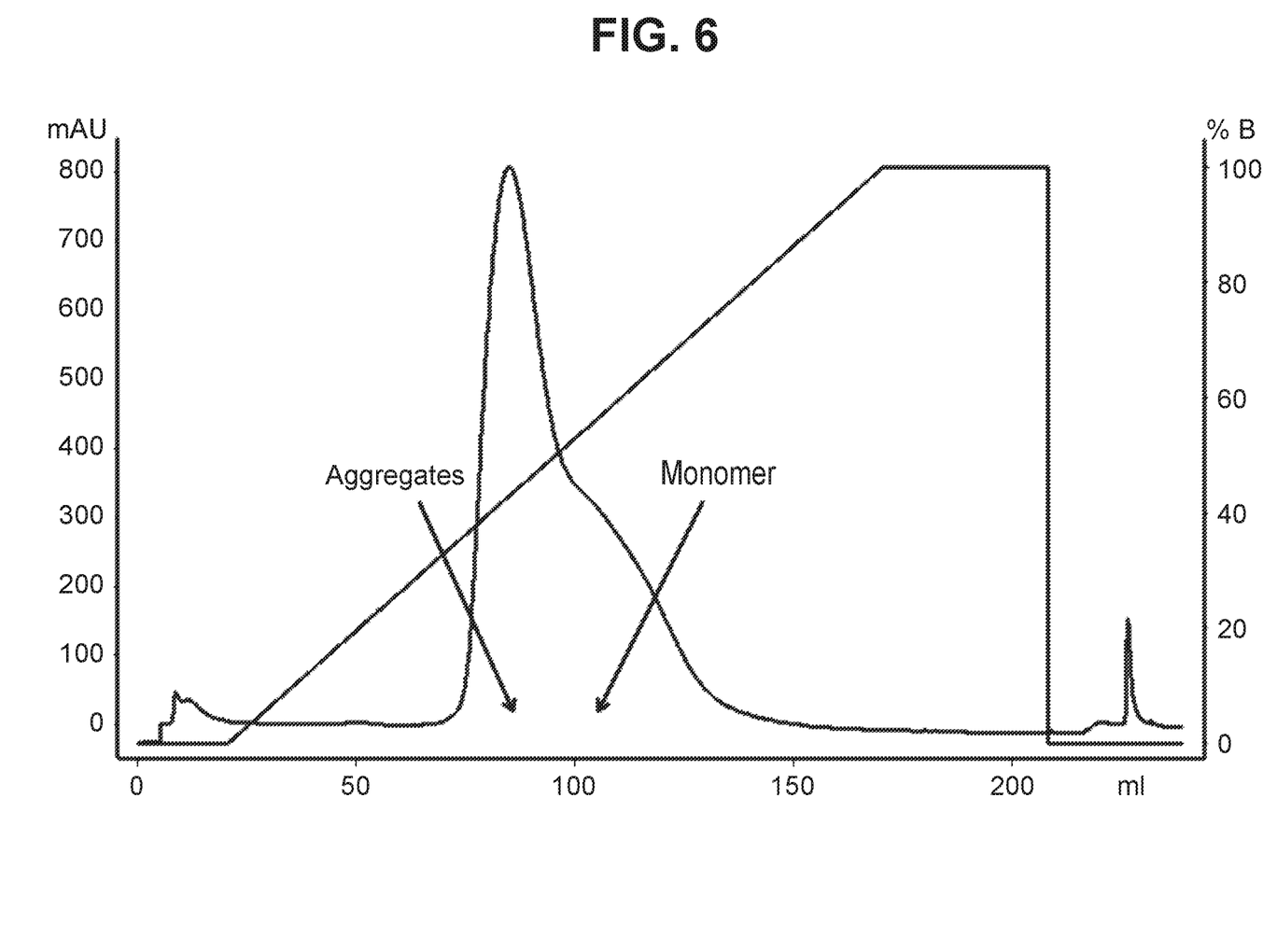
FIG. 6 shows the purification of a Notch 3 ADC on a hydroxyapatite resin using a mobile phase containing high concentration of sodium chloride.

Example 16: Purification of Notch 3 ADC on Hydroxyapatite Resin Using Mobile Phase Containing High Concentration of Sodium Chloride The conjugation product containing aggregates ~4.5% and DAR ~4 as determined by analytical HIC was purified on hydroxyapatite resin using phosphate/sodium chloride/HEPES buffers. Following conditions were used for the purification process, Mobile phase A: 5 mM sodium phosphate, pH 7; Mobile phase B: 5 mM sodium phosphate, 2M sodium chloride, pH 7; Protein loading=11 mg/mL, Flow rate=1 mL/min, bed height=22 cm, Gradient=0-100% B over 20 column volumes. Several fractions were collected and analyzed by SEC assay for presence of aggregates and by UV assay for the DAR. The early eluting fractions contained most of the aggregates. Fractions containing lower aggregate levels were pooled and evaluated for aggregate and DAR content. The aggregate content of the product pool was 3.6% and the DAR value was purified ADC was 3.8. The ADC product was obtained in 92% yield. Only moderate reduction of ~1% in the aggregate levels was observed compared to the unpurified product. The purification chromatogram is shown in FIG. 6.

We claim:

1. A method for purifying antibody drug conjugate (ADC) monomers from aggregates in an ADC preparation, said method comprising the steps of:
   (i) loading an ADC preparation onto a hydroxyapatite resin column,
   (ii) washing said hydroxyapatite resin column with a sodium phosphate buffer of concentration ranging from about 5 to about 35 mM; and
   (iii) eluting said ADC preparation through said column with a sodium phosphate buffer of gradually increasing concentration,
     wherein the concentration of sodium phosphate in said sodium phosphate buffer of step (iii) is initially about 20-25 mM and is increased to about 140 mM,
   whereby purified ADC monomers are separated from said aggregates.

2. The method of claim 1, wherein said purified ADC preparation contains less than 5% aggregates.

3. The method of claim 1, wherein said purified ADC preparation is at least 95% ADC monomer.

4. The method of claim 1, wherein said sodium phosphate buffer used in step (iii) has a pH from about 6.8 to about 7.5.

5. The method of claim 1, wherein the volume of said sodium phosphate buffer used in step (ii) is about 1-5 column volumes.

6. The method of claim 1, wherein the volume of said sodium phosphate buffer used in step (iii) is about 5-25 column volumes.

7. The method of claim 1, wherein the antibody component of said ADC preparation is monoclonal, polyclonal, chimeric, humanized, or a fragment thereof.

8. The method of claim 1, wherein said resin is ceramic hydroxyapatite type I or type II.

9. The method of claim 1, wherein said ADC preparation is first subjected to ion or anion exchange chromatography.

10. The method of claim 1, wherein said purified ADC monomer contains an average DAR of between 3 and 5.

11. The method of claim 1, wherein said purified ADC monomer contains an average DAR of between 3.5 and 4.5.

12. The method of claim 1, wherein said ADC preparation comprises an anti-Notch 3 antibody and an auristatin payload.

13. The method of claim 1, wherein said ADC is an anti-Notch 3 ADC of the formula:

where X is an anti-Notch 3 antibody.

14. The method of claim 1, wherein said ADC preparation contains an organic solvent.

15. The method of claim 14, wherein said solvent is dimethyl sulfoxide (DMSO).

16. The method of claim 1, wherein said ADC preparation contains one or more additional impurities selected from unconjugated payload molecules, species originating from the payload, quench reagents, reducing agents, and reducing agent byproducts.

* * * * *